United States Patent [19]

Varie et al.

[11] Patent Number: 4,471,123
[45] Date of Patent: Sep. 11, 1984

[54] SYNTHESIS OF ISOXAZOLYL IMIDAZOLIDINONES

[75] Inventors: David L. Varie; John C. Lechleiter, both of Indianapolis, Ind.

[73] Assignee: Eli Lilly and Company, Indianapolis, Ind.

[21] Appl. No.: 490,014

[22] Filed: Apr. 29, 1983

[51] Int. Cl.³ ............................................ C07D 233/02
[52] U.S. Cl. .................................... 548/246; 548/301; 548/245; 548/309; 548/308
[58] Field of Search ............... 548/245, 246, 301, 308, 548/311

[56] References Cited

U.S. PATENT DOCUMENTS 4,067,868  1/1978  Ishizumi .............................. 548/492
4,268,679  5/1981  Lavanish ............................. 548/247

OTHER PUBLICATIONS

Barton and Ollis, *Comprehensive Organic Chemistry*, Pergamon, New York (1979), p. 1039.

Primary Examiner—Donald G. Daus
Assistant Examiner—A. Hendricks
Attorney, Agent, or Firm—Joseph A. Jones; Arthur R. Whale

[57] ABSTRACT

Herbicidal isoxazolyl imidazolidinones are prepared by reaction of an isoxazolyl-allylurea with ozone and reduction.

20 Claims, No Drawings

SYNTHESIS OF ISOXAZOLYL IMIDAZOLIDINONES

BACKGROUND OF THE INVENTION

1. Field of the Invention

This invention belongs to the field of agricultural chemistry, and provides a superior process for preparing a series of isoxazolyl imidazolidinones, which are known herbicides, as taught by Lavanish in U.S. Pat. No. 4,268,679.

2. State of the Art

The compounds prepared by the present invention are all taught by Lavanish, who disclose their synthesis by several process variations. One process (columns 19-20 of the patent) proceeds by the cyclization of a substituted isoxazolylurea, where the urea moiety terminates in a dialkyl acetal. That compound was cyclized at elevated temperature in aqueous acid, which process is quite different from the present oxidation of an allylurea with ozone followed by reduction, which provides very excellent yields of relatively pure products.

SUMMARY OF THE INVENTION

The present invention provides a process for preparing an isoxazolyl imidazolidinone of the formula

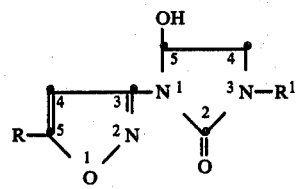

wherein R is $C_3$–$C_6$ branched alkyl or $C_1$–$C_6$ haloalkyl having 1-3 halo atoms; $R^1$ is $C_1$–$C_3$ alkyl; comprising reacting with ozone an isoxazolylurea of the formula

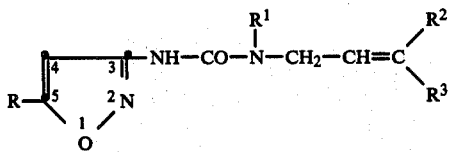

wherein $R^2$ and $R^3$ independently represent hydrogen, phenyl, benzyl or $C_1$–$C_7$ alkyl; and reducing the resulting oxidized intermediate.

DESCRIPTION OF THE PREFERRED EMBODIMENTS

All temperatures in the document are described in degrees Celsius.

It is believed that the nature of the products prepared by the present invention is entirely understandable, but a few typical products will be mentioned to assure that the reader comprehends the invention without difficulty.

1-(5-isopropylisoxazol-3-yl)-3-ethyl-5-hydroxy-2-oxoimidazolidine
1-(5-isobutylisoxazolyl-3-yl)-5-hydroxy-3-propyl-2-oxoimidazolidine
1-(5-s-butylisoxazol-3-yl)-5-hydroxy-3-isopropyl-2-oxoimidazolidine
1-(5-t-butylisoxazol-3-yl)-3-ethyl-5-hydroxy-2-oxoimidazolidine
1-(5-neopentylisoxazol-3-yl)-5-hydroxy-3-methyl-2-oxoimidazolidine
1-[5-(1-methylbutyl)isoxazol-3-yl]-5-hydroxy-3-methyl-2-oxoimidazolidine
1-[5-(1-ethylpropyl)isoxazol-3-yl]-5-hydroxy-3-methyl-2-oxoimidazolidine
1-[5-(3-methylbutyl)isoxazol-3-yl]-5-hydroxy-3-propyl-2-oxoimidazolidine
1-[5-(1-methylpentyl)isoxazol-3-yl]-3-ethyl-5-hydroxy-2-oxoimidazolidine
1-[5-(1,1-dimethylbutyl)isoxazol-3-yl]-5-hydroxy-3-isopropyl-2-oxoimidazolidine
1-(5-trifluoromethylisoxazol-3-yl)-5-hydroxy-3-methyl-2-oxoimidazolidine
1-[5-(4-methylpentyl)isoxazol-3-yl]-5-hydroxy-3-methyl-2-oxoimidazolidine
1-[5-(2-fluoroethyl)isoxazol-3-yl]-3-methyl-5-hydroxy-2-oxoimidazolidine
1-[5-(2-bromoisopropyl)isoxazol-3-yl]-5-hydroxy-3-methyl-2-oxoimidazolidine
1-[5-(1,3-dichloroisopropyl)isoxazol-3-yl]-5-hydroxy-3-propyl-2-oxoimidazolidine
1-[5-(1-chloromethyl-1-methylethyl)isoxazol-3-yl]-5-hydroxy-3-isopropyl-2-oxoimidazolidine
1-[5-(1,1,2-trifluorobutyl)isoxazol-3-yl]-5-hydroxy-3-methyl-2-oxoimidazolidine
1-[5-(2,2-dibromoisobutyl)isoxazol-3-yl]-5-hydroxy-3-methyl-2-oxoimidazolidine
1-[5-(5-chloropentyl)isoxazol-3-yl]-5-hydroxy-3-isopropyl-2-oxoimidazolidine
1-[5-(1-ethyl-3,3,3-trifluoropropyl)isoxazol-3-yl]-3-ethyl-5-hydroxy-2-oxoimidazolidine
1-[5-(2,2-bis[bromomethyl]propyl)isoxazol-3-yl]-3-propyl-5-hydroxy-2-oxoimidazolidine
1-[5-(4-chlorohexyl)isoxazol-3-yl]-5-hydroxy-3-methyl-2-oxoimidazolidine
1-[5-(4,4,4-trichloro-1,1-dimethylbutyl)isoxazol-3-yl]-5-hydroxy-3-methyl-2-oxoimidazolidine
1-[5-(1-ethyl-3,4,4-trifluorobutyl)-5-hydroxy-3-methyl-2-oxoimidazolidine The generally named groups in the structural formulae above have their usual meanings in organic chemistry. For example, the term $C_3$–$C_6$ branched alkyl is used to refer to such groups as isopropyl, t-butyl, isobutyl, neopentyl, 1-ethylpropyl, 1-ethyl-1-methylpropyl, 3-methylpentyl and the like. The terms $C_1$–$C_3$ alkyl and $C_1$–$C_7$ alkyl are used to include such groups as methyl, ethyl, propyl, isopropyl, butyl, s-butyl, 2-methylbutyl, pentyl, hexyl, 2,3-dimethylbutyl, heptyl, 2-ethylbutyl, 1-propylbutyl, 5-methylhexyl and the like.

The term $C_1$–$C_6$ haloalkyl having 1-3 halo atoms refers to groups such as trifluoromethyl, trichloromethyl, 2,2,2-tribromoethyl, 2-fluoroisopropyl, chloro-t-butyl, 3,3-dichlorobutyl, 1-chloro-2-methylbutyl, 4,4,4-tribromobutyl, 2-ethyl-3-fluorobutyl, 1,1-dichlorohexyl and the like.

The $R^2$ and $R^3$ groups on the starting compound have no effect on the product, because they are lost in the reaction. The starting compound, thus, is chosen according to economy and convenience in the circumstances. A few typical starting compounds will be mentioned to assure clarity.

1-(5-t-butylisoxazol-3-yl)-3-methyl-3-(3-phenylallyl)urea
1-(5-trifluoromethylisoxazol-3-yl)-3-ethyl-3-(3-methylbuten-2-yl)urea 1-(5-isobutylisoxazol-3-yl)-3-methyl-3-(4-phenylbuten-2-yl)urea 1-(5-t-butylisoxazol-3-yl)-3-methyl-3-(4-methylpenten-2-yl)urea 1-(5-trichloromethylisoxazol-3-yl)-3-ethyl-3-(hepten-2-yl)urea 1-(5-isopropylisoxazol-3-yl)-3-methyl-3-(3-methylocten-2-yl)urea 1[5-(4-methylpentyl)isoxazol-3-yl]-3-ethyl-3-(5-methylocten-2-yl)urea 1-(5-t-butylisoxazol-3-yl)-3-methyl-3-(3-methyl-4-phenylbuten-2-yl)urea 1-(5-isopropylisoxazol-3-yl)-3-methyl-3-(8-methylnonen-2-yl)urea The synthesis of such isoxazolylureas was shown by Yukinaga et al. in U.S. Pat. No. 4,062,861. Example 131 of that patent, for example, shows one of the present starting materials where R is isobutyl and $R^1$ is methyl. All of the starting materials are easily prepared by common methods known to organic chemists.

Certain groups of products of the present invention are particularly preferred. Preferred groups of products are defined by the following limited definitions of the substituent groups. The preferred definitions of the three substituent groups may be combined to form further, more limited preferred groups of products.

(a) R is α-branched alkyl;
(b) R is bis(α-branched)alkyl;
(c) R is α-branched haloalkyl;
(d) R is bis(α-branched)haloalkyl;
(e) R is trihalomethyl;
(f) $R^1$ is methyl.

The products of the present process are herbicides, and their methods of use are taught by U.S. Pat. No. 4,268,679.

The process of the present invention is carried out by oxidizing the starting compound with ozone, and reducing the resulting oxidized intermediate. Ozone may be supplied to the process in the usual way, diluted with air as it is formed in typical ozonators. It has been found that no particular excess of ozone is necessary, if the air-ozone mixture is efficiently dispersed in the reaction mixture with good agitation. Chemists usually monitor reactions with ozone by testing the off-gas from the reactor with an indicator such as starch/iodine paper, and adjusting the addition rate of the ozone to minimize wasting it. Completion of the reaction is easily observed in the same way, because it is signaled by a sudden increase in the concentration of ozone leaving the reactor.

No particular precautions need be observed in the ozone reaction, except that reaction mixtures have often been observed to foam vigorously as the reaction proceeds. Adequate head space in the reactor must be allowed to accommodate foaming; small amounts of antifoam materials such as silicones may be used.

After the oxidation with ozone is complete, the mixture is reduced by adding a sufficient amount of reducing agent to reduce residual ozone dissolved in the mixture, and to reduce the oxidized intermediate itself. In general, from about 1.1 to about 2.0 equivalents of reducing agent should be added per mole of starting compound. The usual types of reducing agents are used for the reduction. It is unnecessary to use catalytic or electrolytic reduction; inexpensive reducing agents such as $C_1$-$C_4$ dialkyl sulfides, thiosulfate salts, sulfite salts, hydrosulfite salts, alkali metal iodides, sulfur dioxide, stannous chloride, zinc or magnesium metal, formaldehyde and the like are entirely satisfactory. Dialkyl sulfides, especially dimethyl sulfide, are most preferred.

The process is carried out in an organic solvent which is inert to the oxidizing and reducing agents. Solvents such as halogenated alkanes, lower alkanols, alkyl ketones, aromatics, esters and the like may be used as is convenient in the circumstances. It is preferred to use a water-immiscible solvent, or a substantial amount (at least enough to dissolve the product) of a water-immiscible solvent, if a solvent mixture is used, to facilitate isolation of the product. Relatively minor amounts of lower alkanoic acids or water may also be used in the mixture. Useful specific solvents include, for example, dichloromethane, 1,2-dichloroethane, methanol, isopropanol, methyl ethyl ketone, methyl isobutyl ketone, diisopropyl ketone, ethyl acetate, 1,1,2-trichloroethane, benzene, toluene, propyl butyrate, ethylbenzene and the like. Particularly preferred solvents are mixtures of halogenated alkanes and alkanols, especially dichloromethane/methanol mixtures.

Both the oxidation and reduction steps are preferably carried out in the same solvent, by merely adding the reducing agent to the mixture.

The oxidation step is preferably carried out at a relatively low temperature, in the range of from about −100° to about −50°. Good results are obtained, however, at temperatures in the broad range from about −100° to about the ambient temperature. It is not necessary to use a reduced temperature during the reduction step, however, and the mixture may be allowed to warm to ambient, or even to be moderately heated in the range from about the ambient temperature to about 90°, while the reducing agent is added and the reduction is carried out.

Both steps of the process are quite rapid. The speed of the oxidation step is apparently limited only by the speed with which the ozone can be dispersed and dissolved in the reaction mixture, and the reduction step is also very quick.

The yields obtained by the present process are quite high, as shown by the examples below, and the isolation of the product is simple. In general, the reaction mixture can be layered with water after the reduction is complete, and the product isolated from the organic layer by simple evaporation of solvent.

Following examples further illustrate the process and its advantages.

EXAMPLE 1

1-(5-t-butylisoxazol-3-yl)-5-hydroxy-3-methyl-2-oxoimidazolidine

To a 100 ml. round bottom flask equipped with a magnetic stirring bar and a gas dispersion tube were added 8.89 g. of 1-(5-t-butylisoxazol-3-yl)-3-allyl-3-methylurea, 38 ml. of methanol and 38 ml. of dichloromethane. The solution was cooled to −10°, and approximately 40 millimoles of ozone was introduced into the mixture through the gas dispersion tube in a stream of dry air with good mixing over 1 hour. The temperature of the mixture gradually warmed to about 3° as the reaction went on. When all of the ozone had been added, 5 ml. of dimethyl sulfide was added, and the cooling bath was removed. The temperature of the mixture rose to 32°, and then returned to ambient temperature after 1 hour of stirring. The solvent was then removed from the reaction mixture under vacuum at 35°, reducing the volume to about 15 ml. To the semi-solid was added 100 ml. of water, and the mixture was stirred for 15 minutes and filtered. The filter cake was washed with two 50 ml. portions of additional water, and the solids were dried under vacuum to obtain 8.06 g. of product, m.p. 173°–177°. It contained 0.1% water by Karl Fischer analysis, and its nuclear magnetic resonance spectrum, determined in CDCl$_3$ on a 60 mHZ instrument, showed features at δ 6.60 (s, 1H); 5.82 (1H, X of ABX, $J_{AX}$=7.8 Hz, $J_{BX}$=2.2 Hz); 4.50 (bs, 1H, exchanges with D$_2$O), 3.83–3.23 (2H, AB of ABX, $J_{AB}$=3 Hz); 2.90 (s, 3H); 1.32 (s, 9H). Its infra-red spectrum (KBr pellet) showed bands at 3411 (m), 1699 (s), 1599 (m), 1517 (m), 1500 (m), 1479 (m), 1443 (m), 1402 (m) and 1277 (m) cm$^{-1}$. A 5 g. sample of the above product was recrystallized from 25 ml. of boiling denatured ethanol to obtain 4.2 g. of purified product, m.p. 176°–179°. Its calculated elemental analysis was 55.22% C, 7.16% H, 17.56% N; the actual analysis was 55.49% C, 7.27% H, 17.28% N.

EXAMPLE 2

1-(5-t-butylisoxazol-3-yl)-5-hydroxy-3-methyl-2-oxoimidazolidine

An 0.95 g. portion of 1-(5-t-butylisoxazol-3-yl)-3-allyl-3-methylurea was dissolved in 40 ml. of 1:1 by volume methanol:dichloromethane, and the solution was cooled to −5°. It was stirred vigorously at constant temperature while ozone diluted in dry air was bubbled through the solution for 30 minutes. The amount and concentration of ozone were not measured in this experiment, but the experiment was followed by thin layer chromatography and the ozonation was stopped when the starting compound could no longer be seen by tlc (1:1 hexane:ethyl acetate on silica gel). To the mixture was then added 5 ml. of water, and small amounts of sodium thiosulfate were added with constant stirring until starch/iodine paper showed no indication that ozonides were still present. Then 20 ml. of water and 20 ml. of dichloromethane were added, the mixture was shaken well and the layers were separated. The aqueous layer was extracted with 30 ml. of dichloromethane, and the organics were combined, washed with 25 ml. of water, dried over magnesium sulfate and evaporated under vacuum at 30° to obtain 0.69 g. of a white solid. Its melting point was 157°–170°. Analysis by nmr in CDCl$_3$ on a 60 mHz instrument showed that the product was substantially identical with that of Example 1. The product was recrystallized from ethyl acetate:methylcyclopentane to obtain 0.4 g. of white crystalline product, m.p. 174°–176°.

EXAMPLE 3

1-(5-t-butylisoxazol-3-yl)-5-hydroxy-3-methyl-2-oxoimidazolidine

A 4.74 g. portion of 1-(5-t-butylisoxazol-3-yl)-3-allyl-3-methylurea was dissolved in 50 ml. of methanol, and was cooled to −12°. Ozone-containing air was bubbled through the mixture with good stirring for 80 minutes. The temperature rose as high as 0° during the ozone addition, and the mixture foamed and left solids on the flask walls above the liquid. It was necessary to wash the solid down with 20 ml. of additional methanol. Ten ml. of additional methanol was used to wash the gas frit when it began to plug from precipitated product. After the addition was complete, nitrogen was bubbled through the solution for 5 minutes, and then 1.5 ml. of dimethyl sulfide was added and the mixture was warmed to 20° and diluted with 80 ml. of water. The methanol was removed under vacuum at 40°, and the remaining mixture was filtered and the solids were washed with 50 ml. of water and dried under vacuum at 50° to obtain 2.68 g. of the desired product, m.p. 173°–176°. It was further identified by nmr analysis which showed it to be substantially identical to the product of Example 1.

EXAMPLE 4

1-(5-t-butylisoxazol-3-yl)-5-hydroxy-3-methyl-2-oxoimidazolidine

A 2.96 g. portion of 1-(5-t-butylisoxazol-3-yl)-3-allyl-3-methylurea was dissolved in 25 ml. of 1:1 by volume dichloromethane:methanol, and the solution was cooled to −78°. Ozone diluted in dry air was bubbled into the solution with good stirring for 30 minutes, after which tlc analysis indicated that the starting material was gone. Nitrogen was bubbled through the mixture for 10 minutes to remove residual dissolved ozone, and then 1 ml. of dimethyl sulfide was added and the mixture was allowed to warm to ambient temperature with continual stirring. The reaction mixture was then diluted with water, the layers were separated, and the product was isolated from the organic layer substantially as shown in Example 2 above to obtain 2.6 g. of the desired product, m.p. 168°–174°. The nuclear magnetic resonance analysis of the product indicated that it was substantially identical to that of Example 1 above.

EXAMPLE 5

1-(5-t-butylisoxazol-3-yl)-5-hydroxy-3-methyl-2-oxoimidazolidine

The process of this example was carried out substantially identically to that of Example 4, except that the solvent was 25 ml. of 4:1 methanol:dichloromethane. A 2.35 g. portion of the desired product, m.p. 169°–177°, was obtained. A small portion of the product was recrystallized from boiling ethanol to obtain highly purified product, m.p. 173.5°–176°. Its elemental analysis was 55.26% C, 7.26% H, 17.28% N.

EXAMPLE 6

1-(5-t-butylisoxazol-3-yl)-5-hydroxy-3-methyl-2-oxoimidazolidine

An 8.89 g. portion of 1-(5-t-butylisoxazol-3-yl)-3-allyl-3-methylurea was dissolved in 75 ml. of 1:1 by volume dichloromethane:methanol, and a few mg. of Sudan III dye was added. The solution was stirred well at ambient temperature while air/ozone was bubbled in through a coarse frit. A small amount of a silicone antifoam was added and was found to substantially decrease the foaming problem. After 55 minutes of ozone addition, 10 ml. of additional dichloromethane was added to dissolve a precipitate. The color was discharged from the mixture after 65 minutes, and the ozone flow was then stopped and 5 ml. of dimethyl sulfide was added. The temperature rose to 48° over 5 minutes, and the mixture was stirred for 1 hour while the temperature returned to ambient. Solvent was then removed under vacuum at 35°, until the first precipitate was observed. One hundred ml. of water was then added and the mixture was stirred for 15 minutes and filtered. The solids were washed with 50 ml. of water and dried for 16 hours under vacuum at 50° to obtain 7.52 g. of product, which was recrystallized by dissolving it in 35 ml. of 80° isopropanol and cooling at 0° for 3 hours. The precipitated solids were dried to obtain 6.65 g. of snow-white product, m.p. 177°–179°. Analysis of the product by nmr indicated that it was substantially identical to the product of Example 1.

EXAMPLE 7

1-(5-t-butylisoxazol-3-yl)-5-hydroxy-3-methyl-2-oxoimidazolidine

A 2.37 g. portion of 1-(5-t-butylisoxazol-3-yl)-3-allyl-3-methylurea was dissolved in 50 ml. of dichloromethane:methanol:acetic acid, 75:20:5 by volume. The solution was cooled to −78°, and air/ozone was bubbled in through a coarse frit at constant temperature with good stirring. When a blue color appeared in the solution, the ozone flow was stopped, and nitrogen was bubbled through for 10 minutes. Then 1 ml. of dimethyl sulfide was added and the mixture was warmed to ambient temperature. Then 25 ml. of water was added, the mixture was stirred for 30 minutes, and the aqueous layer was separated and extracted 3 times with 25 ml. portions of dichloromethane. The organic layers were combined, dried over sodium sulfate, and evaporated to dryness under vacuum to obtain 2.58 g. of solid, which was slurried in 25 ml. of diethyl ether. The solids were dried to obtain 1.95 g. product, m.p. 174°–177°, substantially identical to the product of Example 1 by tlc analysis.

I claim:

1. A process for preparing an isoxazolyl imidazolidinone of the formula

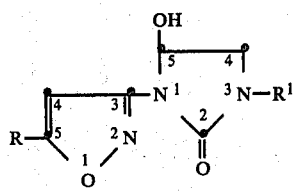

wherein R is $C_3$–$C_6$ branched alkyl or $C_1$–$C_6$ haloalkyl having 1-3 halo atoms; $R^1$ is $C_1$–$C_3$ alkyl; comprising reacting with ozone an isoxazolylurea of the formula

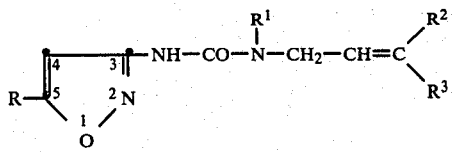

wherein $R^2$ and $R^3$ independently represent hydrogen, phenyl, benzyl or $C_1$–$C_7$ alkyl; and reducing the resulting oxidized intermediate.

2. A process of claim 1 wherein the product is a compound wherein R is α-branched alkyl.

3. A process of claim 2 wherein the product is a compound wherein R is bis(α-branched alkyl).

4. A process of claim 1 wherein the product is a compound wherein R is trifluoromethyl.

5. A process of claim 3 wherein the product is a compound wherein R is t-butyl.

6. A process of claim 1 wherein the product is a compound wherein $R^1$ is methyl.

7. A process of claim 2 wherein the product is a compound wherein $R^1$ is methyl.

8. A process of claim 4 wherein the product is a compound wherein $R^1$ is methyl.

9. A process of claim 5 wherein the product is a compound wherein $R^1$ is methyl.

10. A process of claim 1 which is carried out in the presence of a substantial amount of a water-immiscible solvent.

11. A process of claim 2 which is carried out in the presence of a water-immiscible solvent.

12. A process of claim 4 which is carried out in the presence of a water-immiscible solvent.

13. A process of claim 5 which is carried out in the presence of a water-immiscible solvent.

14. A process of claim 9 which is carried out in the presence of a water-immiscible solvent.

15. A process of claim 1 wherein the reduction is carried out with a $C_1$–$C_4$ dialkyl sulfide.

16. A process of claim 10 wherein the reduction is carried out with a $C_1$–$C_4$ dialkyl sulfide.

17. A process of claim 11 wherein the reduction is carried out with a $C_1$–$C_4$ dialkyl sulfide.

18. A process of claim 13 wherein the reduction is carried out with a $C_1$–$C_4$ dialkyl sulfide.

19. A process of claim 14 wherein the reduction is carried out with a $C_1$–$C_4$ dialkyl sulfide.

20. A process of claim 14 wherein the reduction is carried out with dimethyl sulfide.

* * * * *